(12) United States Patent
Cohen

(10) Patent No.: US 8,893,720 B2
(45) Date of Patent: Nov. 25, 2014

(54) INHALATION APPARATUS

(76) Inventor: Binyomin A. Cohen, Brooklyn, NY (US)

(*) Notice: Subject to any disclaimer, the term of this patent is extended or adjusted under 35 U.S.C. 154(b) by 255 days.

(21) Appl. No.: 13/027,574

(22) Filed: Feb. 15, 2011

(65) Prior Publication Data

US 2012/0204872 A1 Aug. 16, 2012

(51) Int. Cl.
*A62B 18/02* (2006.01)
*A61M 15/08* (2006.01)
*A62B 7/00* (2006.01)
*A61M 16/12* (2006.01)
*A61M 16/06* (2006.01)

(52) U.S. Cl.
CPC ........... *A61M 16/12* (2013.01); *A61M 16/0666* (2013.01); *A61M 16/127* (2013.01); *A61M 2202/0208* (2013.01)
USPC .................................. 128/207.13; 128/207.18

(58) Field of Classification Search
USPC ............. 128/204.18, 204.24, 204.25, 205.11, 128/205.25, 206.21, 207.13, 207.18
See application file for complete search history.

(56) References Cited

U.S. PATENT DOCUMENTS

| | | | | |
|---|---|---|---|---|
| 1,443,820 A | * | 1/1923 | Hudson | 128/202.13 |
| 2,647,511 A | | 8/1953 | Barach | |
| 2,792,000 A | | 5/1957 | Richardson | |
| 3,012,694 A | * | 12/1961 | Johnston | 222/5 |
| 3,754,552 A | | 8/1973 | King | |
| 3,902,486 A | * | 9/1975 | Guichard | 128/203.22 |
| 4,156,426 A | | 5/1979 | Gold | |
| 4,248,218 A | * | 2/1981 | Fischer | 128/204.18 |
| 4,263,908 A | | 4/1981 | Mizerak | |
| 4,266,540 A | * | 5/1981 | Panzik et al. | 128/207.13 |
| 4,354,488 A | * | 10/1982 | Bartos | 128/205.25 |
| 4,377,162 A | | 3/1983 | Staver | |
| 4,454,880 A | * | 6/1984 | Muto et al. | 128/205.25 |
| 4,655,213 A | * | 4/1987 | Rapoport et al. | 128/205.25 |
| 7,255,107 B1 | * | 8/2007 | Gomez | 128/207.13 |
| 2007/0227541 A1 | * | 10/2007 | Van den Akker et al. | 128/205.24 |
| 2009/0095298 A1 | * | 4/2009 | Gunaratnam et al. | 128/204.18 |
| 2010/0139664 A1 | * | 6/2010 | Curti et al. | 128/207.18 |

FOREIGN PATENT DOCUMENTS

| | | |
|---|---|---|
| CA | 503739 | 6/1954 |
| FR | 765228 | 6/1934 |

* cited by examiner

*Primary Examiner* — Kristen Matter
(74) *Attorney, Agent, or Firm* — Ladas & Parry LLP

(57) ABSTRACT

An inhalation device which entrains air to modify a source gas, such as pure oxygen, down to different selected levels of lower gas concentrations, with a high total gas flow being achieved for inhalation. The inhalation device allows eating and suctioning without interference while maintaining a constant uninterrupted gas supply at high volumes. The inhalation device is adapted for disposal adjacent to the nose and mouth of a person, and includes a nose hood connected to a chamber. The chamber has a central portion defining a longitudinal axis orientated perpendicular to the nose hood and also defining an opening aligned with and facing the nose in a configuration such that gas is inhalable from the central portion to the nose without the gas directly impacting the breathing orifices of a patient wearing the device.

30 Claims, 6 Drawing Sheets

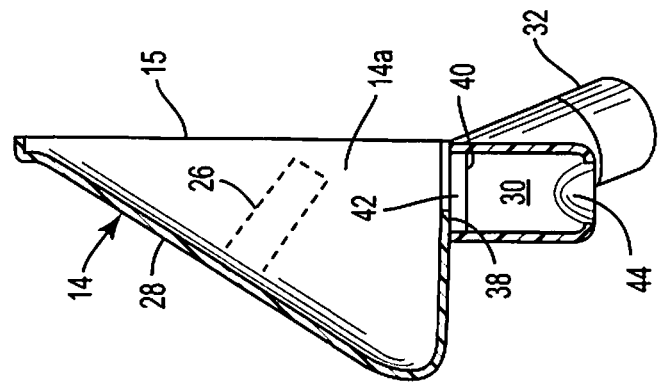
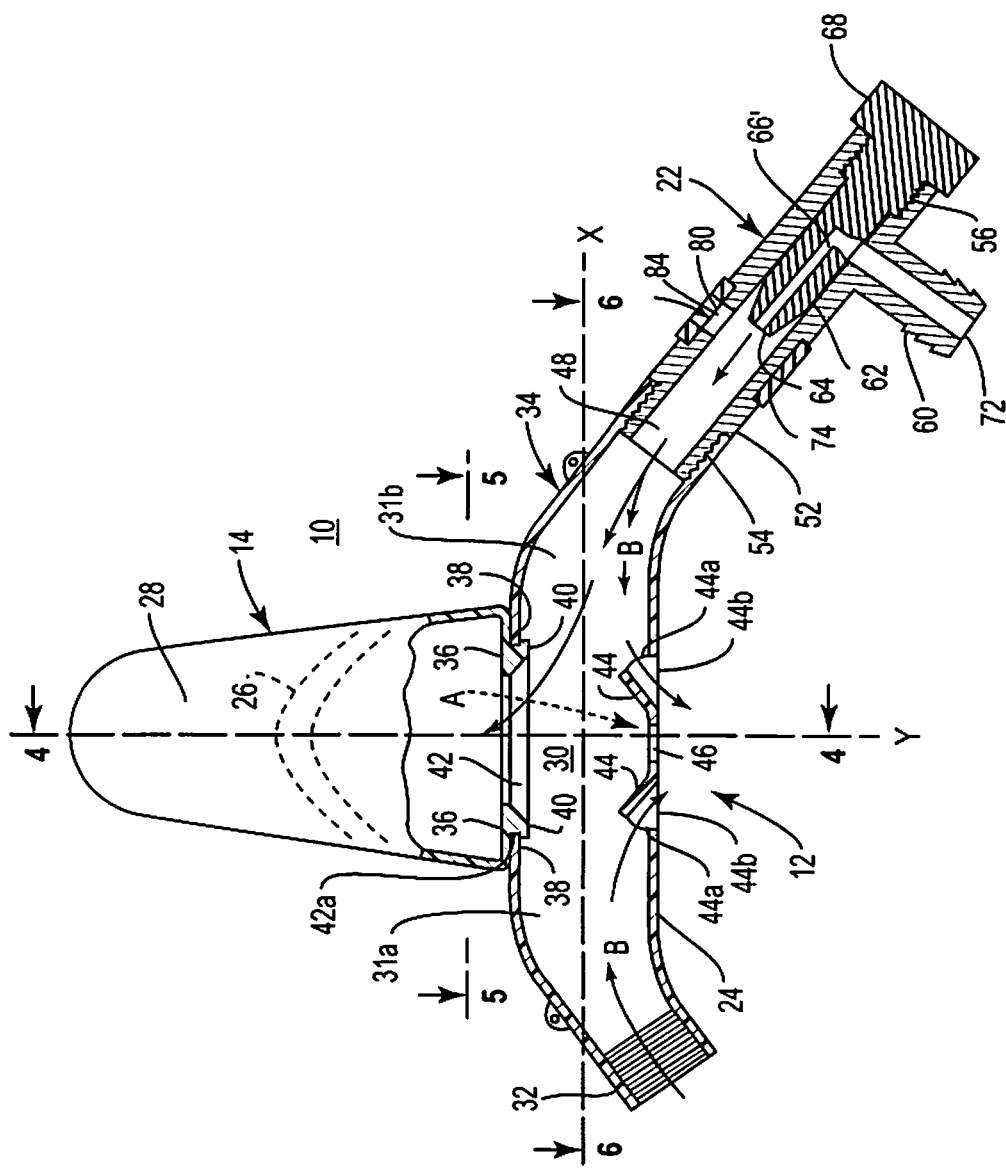
FIG. 4
FIG. 3

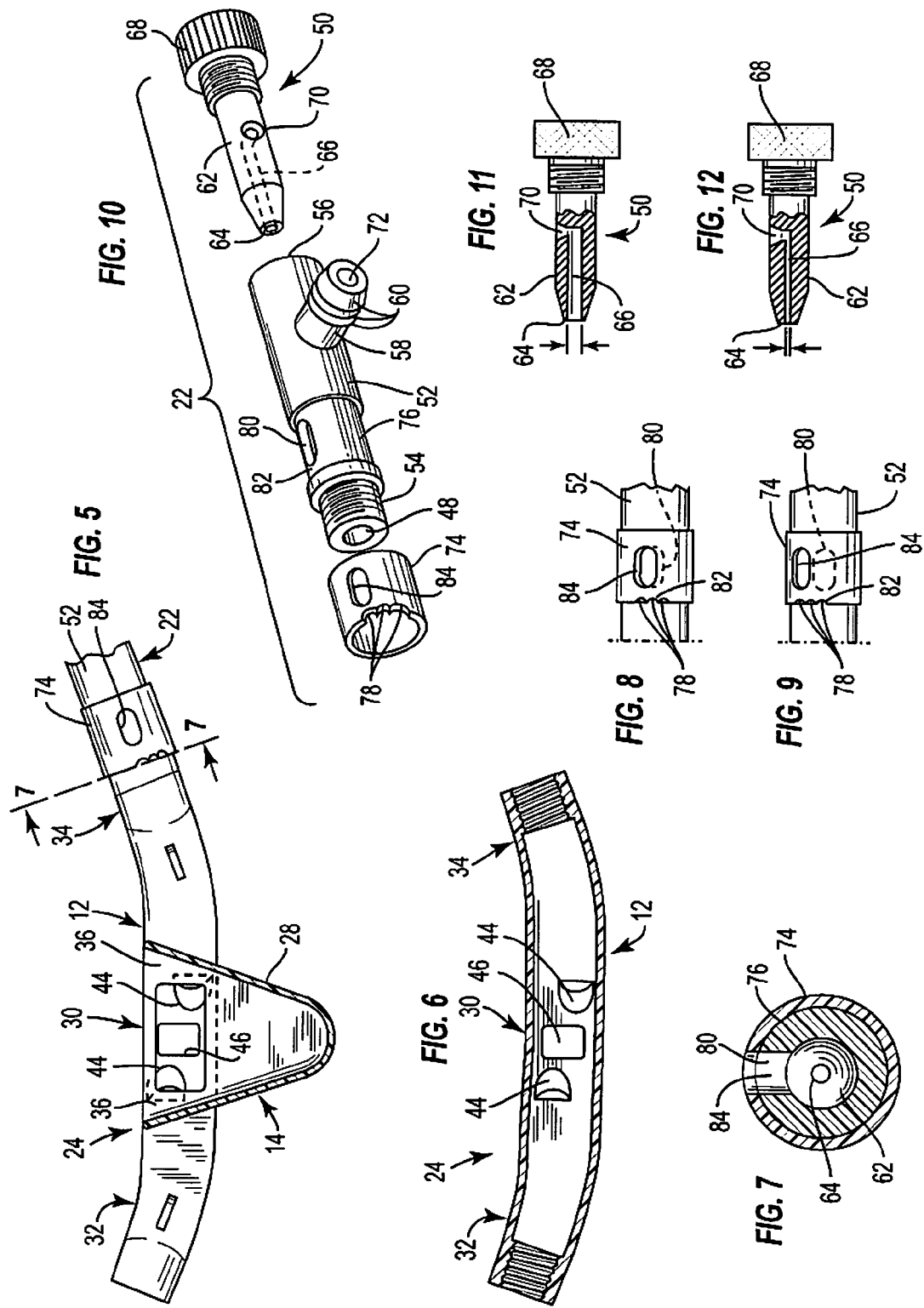

INHALATION APPARATUS

FIELD OF THE INVENTION

The present invention relates generally to the medical arts and in particular to an improved device to supply a mixture of fluids, such as oxygen and ambient air, for inhalation by an individual.

BACKGROUND OF THE INVENTION

In general, the supply of fluids and in particular oxygen, in gaseous form is required in a diverse number of medical situations. Depending on the specific medical condition observed, an enriched supply of oxygen over that of the ambient atmosphere, is often required. Such oxygen is normally supplied through a nasal cannula, which consists of two hollow prongs, each of which is inserted into a nasal nostril. The cannula is connected to a source of pure oxygen through a humidifying device, which allows the dry oxygen to be supplied with water or water vapor.

Other methods of providing oxygen to a patient utilize a variety of masks, such as a Venturi® mask, which cover both the nose and mouth of the wearer. In both the nasal cannula and/or mask designs, however, the gas is forced directly into the nose and/or mouth, with numerous drawbacks. First, depending upon the flow rate of the gas, the pressure of the impinging gas upon the relatively sensitive nasal membranes can be irritating and painful, as well as detrimental to the patient's condition. Typically, gas flow rates off Venturi® masks are between 105 liters per minute i.e., "lpm," at the high end and 34 lpm at the low end, which can dry out a normal individual even using a heated humidifier in less than 2 hours. This often has the disadvantageous effect of rapidly drying the moist tissues caused by the nasal cannula and mask designs, which can lead to increased bronchial spasms and airway plugging. The higher the gas flow, the quicker the patient is subjected to tissue drying, desiccation, endothelial bleeding and cracking with associated increased airway plugging, infection and pneumonitis.

Secondly, as Venturi® breathing systems generate high flow rates, even at high concentrations of oxygen where the air mix resulting from air entrainment is low (35 to 50 lpm of flow) and impacts directly onto the patient/user's breathing orifices. Prior art devices direct such flow directly opposing the breathing orifices, resulting in rapid airway lining tissue drying, membrane cracking, bleeding and pain. Major adverse effects can be observed if a Venturi® system's airflow is directed as seen in prior art designs, confined to and into the nasal passages. These effects include severe repetitive nasal bleeding resulting from desiccated and cracked tissues, inspisated secretions of nasal epithelium and submucosa, as well as severe headaches, esophageal air swallowing, vomiting and aspiration, all with deleterious results, including yet not limited to aspiration pneumonitis.

The normal response of a conscious and mobile patient user is to remove the breathing device to alleviate the pain and discomfort resulting from such Venturi® devices, as seen clinically throughout intensive care units and wards. However, in neurologically and/or disabled and/or unconsciously breathing patient/user, the results of leaving such high flow devices as Venturi® masks are often aspiration of induced vomitus, pneumonia and severe hypoxia.

Additionally, in such prior art designs of the Venturi® mask or apparatus, both source gases and entrained air are directly perpendicular; meaning the total airflow produced is opposing the patient/users breathing orifices. As the increased velocity achieved by the Venturi® jet orifice acts on the incoming source gas, it creates an area of reduced pressure immediately post the exiting source gas jetted out—this causes air entrainment mixing with the source gas oxygen, opposite the patient/user's orifices. As such, any and all back pressure, such as resulting from forced expirations, coughing, pursed lip breathing is directed back onto and affects the "Venturi® Jet valves'" function. This, combined with the breathing rhythm changes as typically evidenced in Chronic Obstruction Pulmonary Disease ("COPD") patients, further worsens the conditions the Venturi® mask was specifically designed to treat. This backpressure directed back to and onto the Venturi® jet valve can affect the effective flow rate of the oxygen and change the amount of oxygen available to the patient. Accordingly, the flow rate administered by the medical personnel is distorted. This can lead to erroneous flow data and potentially life-threatening situations.

Further, the use of a conventional mask is often a burden upon the patient and may be uncomfortable to wear. Use of a nasal cannula requires a source of pure oxygen, as well as apparatus for providing a source of water or water vapor. A device for combining such vapor with the oxygen is also required with these prior designs. What is needed is a Venturi® mask system configured to limit back pressure, provide the proper mixture of oxygen and other gases for breathing and to reduce the drying of nasal passages and orifices due to direct flow.

Therefore, what is needed in the field is an inhalation device specifically designed to overcome the disadvantages and drawbacks of the prior art. That is an improved inhalation device and related methods of use, adapted for disposal adjacent a nose and mouth of a subject, to supply a mixture of fluids, such as oxygen and ambient air, for inhalation by the subject.

SUMMARY OF THE INVENTION

One object of the present invention to provide a fluid inhalation device that is lightweight and may be worn by a subject for an extended period of time without discomfort.

Another object of the present invention is to provide a fluid administration system in which the flow of gas does not cause nasal dryness, nasal bleeding, or other discomfort.

In one particular embodiment of the present invention an inhalation device is provided. The inhalation device includes a nose hood defining a cavity, a chamber connected with the nose hood that includes a central portion configured to be disposed below the nose of a subject and adjacent to the mouth. The central portion defines a longitudinal axis, with the chamber being configured to receive incoming gas. This configuration of the device generates a total gas flow post entrainment at an angle of between about 35 degrees and about 70 degrees with respect to the longitudinal axis, and the chamber is orientated substantially perpendicular to the nose hood. The angle with respect to the longitudinal angle can be adjusted so as to provide a range of angles that are customizable to the profile of the patient using the device. The device also contains a mixing section connected with the chamber and at least one fluid, (i.e. oxygen or oxygen mixture), where the mixing section delivers the at least one fluid to a first end portion of the chamber. The inhalation device of the present invention defines the fluid path and is configured so as to direct the at least one fluid in a direction along the longitudinal axis of the central portion, and exit the chamber from a second end portion. The first end and second end portions are coaxially disposed about the longitudinal axis of the chamber. The central portion defines at least one opening aligned with and facing the nose in a configuration such that the at least one fluid of the fluid flow path is inhalable from the central portion into the nose.

In another embodiment of the present invention an inhalation device including an opening configured so as to be oriented below the nose of a subject, and a nose hood configured to define a cavity and a vertical axis is provided. A chamber is connected with the nose hood and includes a first end portion, a second end portion, and a central portion wherein the central portion is configured so that it is disposed below the nose and adjacent to the mouth of a patient. The central portion on the chamber defines a longitudinal axis oriented substantially perpendicular to the vertical axis. The first and second end portions of the chamber are coaxially disposed about the longitudinal axis, where the first end portion extends to a first end of a chamber and the second end portion extends to a second end of the chamber, with the first and second ends are angularly offset from the longitudinal axis. The device also contains a mixing station that is connected with either the first end or the second end of the nose hood and at least one fluid. The mixing section delivers the at least one fluid to the first end in a fluid flow path configured to travel in a direction along the longitudinal path and exit the chamber out the second end. The central portion defines at least one opening that is disposed in flush alignment with an upper wall of the central portion and faces the nose in a configuration so that the at least one fluid of the fluid path is inhalable from the central portion into the nose.

In one particular embodiment of the present invention is directed to an alternate inhalation device. In this embodiment, the inhalation device includes a nose hood defining a cavity that is connected to a chamber that is connected with the nose hood. The nose hood includes a central portion disposed below the nose of a subject and adjacent to the mouth. The central portion defines a longitudinal axis, with the chamber being configured to receive incoming gas, which generates a total gas flow post entrainment at an angle of between about 0 and about 70 degrees with respect to the longitudinal axis, and the chamber is orientated substantially perpendicular to the nose hood. A mixing section is connected with the chamber and at least one fluid, where the mixing section delivers the at least one fluid to a first end portion of the chamber. The fluid path of the at least one fluid is configured to travel in a direction along the longitudinal axis of the central portion, and exit the chamber from a second end portion. The first end and second end portions are coaxially disposed about the longitudinal axis of the chamber. The central portion defines at least one opening aligned with and facing the nose in a configuration such that the at least one fluid of the fluid flow path is inhalable from the central portion into the nose. The first and second ends portions of the chamber are further configured to be interchangeable with one another.

Yet another aspect of the present invention is directed to a method for using the inhalation devices of the present invention. The method includes providing the nose hood cavity of the inhalation device described in the any of the embodiments above, to a patient in need of breathing aid. This method further entails positioning the gas flow post entrainment of the chamber of the inhalation device at an angle of about 35 to about 70 degrees with respect to the longitudinal axis, and adjusting the device so as to adjust the angle so as to provide a fluid flow path that is inhalable from the central portion into the patient's nose at an angle that does not cause the negative side effects of direct air that are associated with the devise of the prior art.

The above embodiments are further described with reference to the figures and detailed description below.

BRIEF DESCRIPTION OF THE DRAWINGS

The above-mentioned and other features and objects of this disclosure, and the manner of attaining them, will become more apparent and the disclosure itself will be better understood by reference to the following description of embodiments of the disclosure taken in conjunction with the accompanying drawings, wherein:

FIG. 3 shows a front sectional view of the inhalation device shown in FIG. 1;

FIG. 4 shows a side sectional view of the inhalation device taken along line 4-4 of FIG. 3;

FIG. 5 shows a top plan view of the inhalation device taken along line 5-5 of FIG. 3;

FIG. 6 shows a sectional plan view of a central section of the inhalation device taken along line 6-6 of FIG. 3;

FIG. 7 shows a sectional view of the inhalation device taken along line 7-7 of FIG. 5;

FIG. 8 shows a cutaway detail view of a fluid adjustment port of the inhalation device shown in FIG. 1, with the port in the partially open position;

FIG. 9 shows a cutaway detail view of the port shown in FIG. 8 with the port in the fully closed position;

FIG. 10 shows an exploded perspective view of a gas mixing and metering portion of the inhalation device shown in FIG. 1;

FIG. 11 shows a detail view of an injection nozzle of the inhalation device shown in FIG. 1, for a first flow rate; and FIG. 12 shows a detail view of an alternate embodiment of an injection nozzle shown in FIG. 11, for a low flow rate.

DETAILED DESCRIPTION OF THE INVENTION

Figure 2:
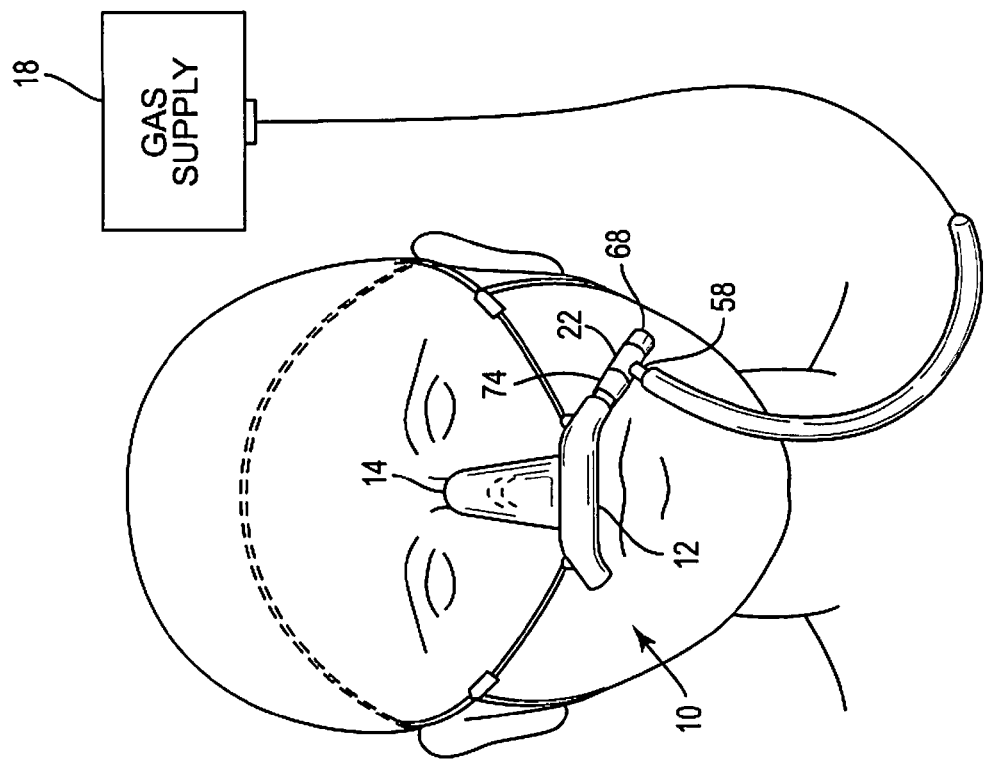
FIG. 2 shows a front perspective view of the inhalation device shown in FIG. 1.

The exemplary embodiments of the inhalation device and methods of use disclosed are discussed in terms of medical apparatus and more particularly, in terms of fluid supply devices, such as oxygen and ambient air, and mixtures thereof that can be employed for inhalation by a subject patient. The inhalation device may be employed for treatment of subjects having conditions requiring increased levels of oxygen. It is envisioned that the present disclosure may be employed with a range of applications including cardiac disease, pulmonary disease and breathing disorders. It is further envisioned that the present disclosure may be used with other medical applications such as diagnosis, treatment and surgery.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The following discussion includes a description of the inhalation device, related components, and exemplary methods of operating the inhalation device in accordance with the principles of the present disclosure. Alternate embodiments are also disclosed. Reference will now be made in detail to the exemplary embodiments of the present disclosure, which are illustrated in the accompanying figures.

In accordance with the above and further objects and purposes, in one particular embodiment, the present invention comprises a generally tubular fluid inhalation unit, which is mounted below the patient's nostrils and between the nose and mouth. The inhalation unit may be affixed to a nose-embracing hood and may be further supported in place by a lightweight cord about the head of the wearer.

The tubular inhalation unit includes a portion in which a first fluid, such as oxygen, is mixed with a second fluid, such as ambient air, in the desired ratio such that the resulting mixture is directed through the inhalation portion of the device. Such inhalation portion has apertures in the wall thereof both facing upwardly towards the nasal cavities and downwardly towards the mouth. While these apertures are located perpendicular to the breathing orifices, the angulations used to isolate the Venturi® jet nozzle from said perpendicular breathing orifices of a patient/user allow a further and greater usage of the designed high gas flow, e.g., post Venturi® jet nozzle and air entrainment mixing that Venture systems used in medicine for COPD patient/users above prior art in two greater beneficial distinct ways.

First, the patient/user is not uncomfortable and does not undergo painful drying of the airways mucosa and bleeding, and allows suctioning and feeding simultaneously, while receiving a properly designed oxygen concentration therapy. Secondly, the surrounding and isolated narrowed region i.e., the 'Venturi® Nozzle Jet' and its reservoir perpendicular to the patient/users breathing orifices protect and provide isolation of back pressure effects to the Venturi® Nozzles Jet function to provide accurate mixed gases even and especially during coughing, pursed lip exhalations, and thus maintaining a greater accurate oxygen concentration through the patient's breathing cycles. The inhalation portion may further be provided with an intermediate bend such that the device closely follows the contour of the face, while providing the patient with tactile indication of operation. Further, it is desirable that the inhalation portion maintains and isolates the mixing chamber from backpressure effects caused by the subject's breathing and without significantly creating undesired backpressure effects.

The present disclosure provides an oxygen administration system having a Venturi® system utilizing source gas. The Venturi® system uses a high flow mixing source gas with ambient gas, typically room air, by a known process called air entrainment. This entrainment of the ambient gases is effected at a restricted aperture as found by forming a jet gas stream.

Such a gas stream is designed to exit a port of the mixing section of the device by which the entering source gas is made to travel through, then said source gas is accelerated through an intentionally designed narrow region to exit a nozzle aperture. This restricted aperture accelerates the gas through such restricted aperture at a higher existing pressure driving said source gas. This innovation differs from the prior art in that the presently disclosed invention, the Venturi® jet nozzle is removed from the direct perpendicular pathway to the patient/users breathing orifices.

Proximal to the restricted aperture, an open window entrains ambient gases, typically room air, at the nozzle. Such increased flow rate acceleration by the source gas affects Bernoulli phenomena.

At the restricted aperture, such gas acceleration causes a pressure drop. The increased source gas flow velocity through such restricted aperture causes a diminution in the local pressure at that point of said restricted aperture. This generates a greater pressure drop immediately existing at the restricted region, allowing the nozzle to entrain ambient air and/or gases by such pressure drop. Such ambient air is driven into the window due to the local pressure drop realized by such greater gas velocity. The ambient gases, room air and the source gas is mixed and delivered to the inhalation portion in known ratios. The entering source gas(es) exits through such nozzle affecting the diminished local pressure at said region exiting the jet nozzles exit.

In the mixing chamber, an air entrainment mixing device using source gas, typically oxygen, is forced through a narrow bore nozzle, depending on the narrow bore nozzle herein called the "Venturi® jet nozzle." Differing bore diameters are used in the art which the invention differs than prior art in this aspect in that prior art uses different caps containing differing narrow bore sizes the invention uses one cap containing differing bore diameters that may be immediately selected as need arises. Thus, a greater cost savings and savings in space of storage and accessibility for the health care practitioner who now no longer needs leave a patient/users bedside to get such prior art caps, he or she may immediately adapt the correct selected bore by simply dialing in the Venturi® jet nozzle of choice. Such entrainment makes usage of the Bernoulli phenomenon of an immediate air pressure drop of the ambient air. For example, a pressure drop of lower than 14.7 PSI at such a jet nozzle exit site is commonly known as the jet Venturi® nozzle. This allows for the higher pressure adjacent the ambient air opening to effect such air entrainment at said jet nozzle. This may also be achieved through the use of pins having a hollow center in each pin, where each pin varies the Venturi® nozzle jet sizes with all said pins having a set fixed inlet size. These pins can be further used to change the narrowed region to allow for differing oxygen concentrations.

In another embodiment, a Venturi® cylinder having a center allowing flow through its center body and by rotating an external collar allows for varying Venturi® jet nozzle sizes encased within said cylinder. This allows for the immediate adjustment of oxygen concentrations and the ability to vary the total gas flow rate without having to break apart the device and remove the patient/user from the Venturi® system, as the prior art requires.

Such entrainment causes the adjacent air surrounding the higher pressure flow to rush into the low pressure region forcing the immediate air about the jet nozzle to enter ports about said jet nozzle. These ports are configured as a Venturi® window. The Venturi® window allows such ports to be opened in varying amounts. Thus, the air is adjustably entrained.

The Venturi® window includes and is actuated by manipulating a shield or sleeve to be varied with an opening of the port, and is placed about the Venturi® jet nozzle region. Depending upon the window size, a quantity of ambient air is entrained, by such pressure drop at said jet nozzle. Assisting such entrainment, ambient air is forced into the opening surrounding the jet nozzle. This Venturi® system process or air entrainment creates a slight vacuum at the surrounding the Venturi® jet nozzle window. The angle is not greater than fifteen degrees, from zero to the port X-axis. Such angle increases the source gas mixed with entrained ambient gases into a larger unrestricted region in the direction of such gas flow through the Venturi® jet nozzle, which is designed to compensate for the increased gas flow rate to protect the patient/user's airways and allow comfortable wearing and the application continued use, critical for the healing and protective measure of such patient/user populations as clinically found in COPD. The increased gas flow rate affects a greater gas flow volume, and gas flow pressure. This configuration facilitates a post restriction conduit with the patient. The result is a product of source gas flowing through the Venturi® small bore nozzle mixed with entrained air, typically at 16 liter/min at a known oxygen percentage.

The present disclosure avoids the drawbacks of the prior art, such as the deleterious effects of imposing a direct high flow gas onto the nasal passages and face, which can result if the flow generated and directed into the patient/users breathing orifices clinically proven to result in drying and cracking effects from even relatively low flows (about 5 lpm) into the nasal passages. Most certainly in higher flow conditions as in Venturi® apparatus used via the prior art which sends 25 lpm and more into the patient's facial breathing orifices.

The present disclosure advantageously provides an inhalation unit, which allows a patient to wear, in one embodiment, a nasal mask using a Venturi® mixing device. The patient, due to the offset angle of the incoming Venturi® high flows, may easily inhale from the available surrounding the mixed source gas. The offset angles designed as described, prevents the downstream backpressure from impacting upon the Venturi® Jet nozzles function, simultaneously allowing the oxygen concentration to remain accurate and preventing against negatively impacting the hypoxic drive mechanism throughout such breathing maneuvers common to the COPD population, of which this mask and Venturi® devices where specifically designed.

In another particular embodiment, in accordance with the principles of the present disclosure, an inhalation device is provided, which is adapted for disposal adjacent a nose and a mouth of a subject breathing orifices, wholly different than prior art which utilizes a Venturi® perpendicular to the breathing orifices with its attendant problems of drying and irritation of the airway mucosa, as well as problems associated with backpressure relayed downstream causing loss of the Venturi® jet nozzle; said Venturi® jet nozzle accomplishes the entrainment of air by a Bernoulli phenomena, to diminish the incoming source gas containing pure 100% oxygen from a flowmeter to a selected lower level concentration for safe oxygen concentrations for inhalation. The inhalation device includes a nose hood defining a cavity. A chamber is connected with the nose hood and includes a central portion disposed below the nose of the subject and adjacent the mouth. The central portion defines a longitudinal axis oriented substantially perpendicular to the nose hood. A mixing section is connected with the chamber and at least one fluid. The mixing section delivers the at least one fluid to a first end portion of the chamber in a fluid flow path configured to travel in a direction along the longitudinal axis of the central portion and exit the chamber from a second end portion thereof. The first end portion and the second end portion are coaxially disposed about the longitudinal axis of the chamber. The central portion defines at least one opening aligned with and facing the nose in a configuration such that the at least one fluid of the fluid flow path is inhalable into the nose.

The first end portion can include a first end, which is angularly offset from the longitudinal axis of the central portion. The second end portion can include a second end, which is angularly offset from the longitudinal axis of the central portion.

The chamber may define at least one scoop configured to divert the at least one fluid of the fluid flow path toward the mouth for inhalation. The chamber may define a pair of opposing scoops that are offset relative to the longitudinal axis of the central portion.

The mixing section can deliver a plurality of fluids to the first end portion. The plurality of fluids may include oxygen provided via a nozzle and ambient air provided via a bore defined with the mixing section. Alternatively, the plurality of fluids may include oxygen provided via a high velocity nozzle across a bore defined within the mixing section causing a fluid pressure drop adjacent the bore such that ambient air is drawn into the mixing section. The oxygen is mixed with the ambient air. An amount of ambient air may be drawn through the bore and is regulated via a sleeve disposed about the mixing section. The nose hood can define a vertical axis and the first end portion and the second end portion are relatively pivotable thereabout.

In an alternate embodiment, the inhalation device includes a nose hood including an opening oriented below the nose. The nose hood defines a cavity and a vertical axis. A chamber is connected with the nose hood and includes a first end portion, a second end portion, and a central portion disposed below the nose and adjacent the mouth. The central portion defines a longitudinal axis oriented substantially perpendicular to the vertical axis. The first end portion and the second end portion are coaxially disposed about the longitudinal axis. The first end extends to a first end of a chamber and the second end portion extends to a second end of the chamber. The first end and the second end each are angularly offset from the longitudinal axis.

A mixing section is connected with either of the first end or the second end, and at least one fluid. The mixing section delivers the at least one fluid to the first end in a fluid flow path configured to travel in a direction along the longitudinal axis and exit the chamber from the second end. The central portion defines at least one opening disposed in flush alignment with an upper wall of the central portion and facing the nose in a configuration such that the at least one fluid of the fluid flow path is inhalable from the central portion into the nose. In an alternate embodiment, the first end and the second end are angularly offset by about 45 degrees from the longitudinal axis. In another embodiment, the chamber defines at least one scoop configured to divert the at least one fluid of the fluid flow path toward the mouth for inhalation. The chamber can define a pair of opposing scoops offset relative to the longitudinal axis of the central portion. The sleeve may be threadably engageable with the mixing section in a configuration for regulating the ambient air drawn through the bore. The first end and the second end can be relatively pivotable about the vertical axis.

Figure 1:
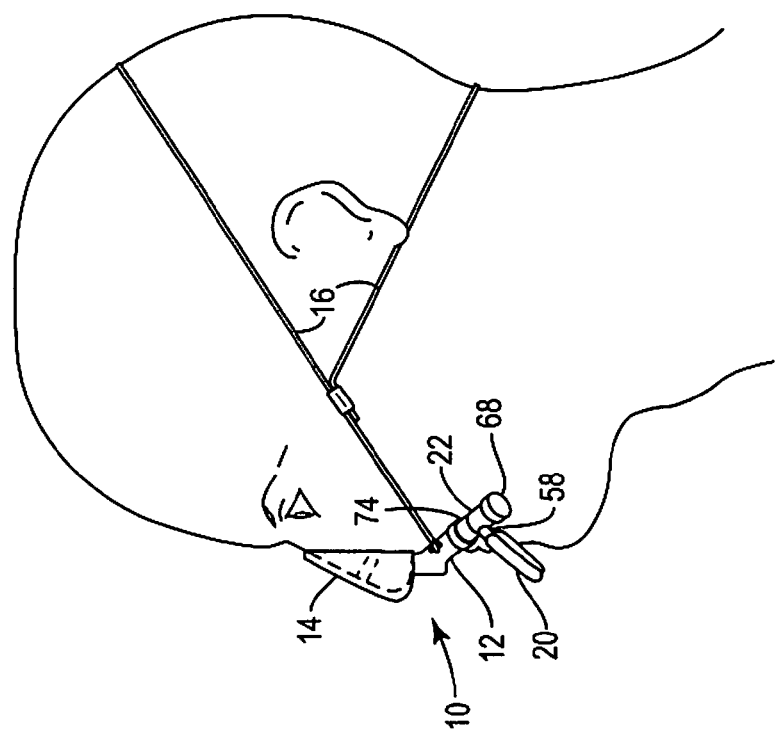
FIG. 1 shows a side perspective view of an inhalation device, in accordance with the principles of the present disclosure, disposed with a subject's face.

Turning now to FIGS. 1 and 2, there is illustrated an inhalation device 10, in accordance with the principles of the present disclosure.

The components of inhalation device 10 are fabricated from materials suitable for medical applications, such as, for example, polymerics and/or metals, depending on the particular application and/or preference. Semi-rigid and rigid polymerics are contemplated for fabrication, as well as resilient materials, such as molded medical grade polyurethane, etc. It is contemplated that any electronics and power components employed with inhalation device 10 may be fabricated from those suitable for a medical application. Inhalation device 10 may also include and/or be connected to circuit boards, circuitry, processor components, etc. for computerized control. One skilled in the art, however, will realize that other materials and fabrication methods suitable for assembly and manufacture, in accordance with the present disclosure, also would be appropriate.

Inhalation device 10 includes a chamber, such as, for example, a tubular shaped fluid mixing and inhalation unit 12 affixed to a semi-rigid nose hood 14. The mixing and inhalation unit 12 and nose hood 14 are retained upon the subject's face by an appropriate elastic banding 16, which encircles the head of the subject.

Figure 16:
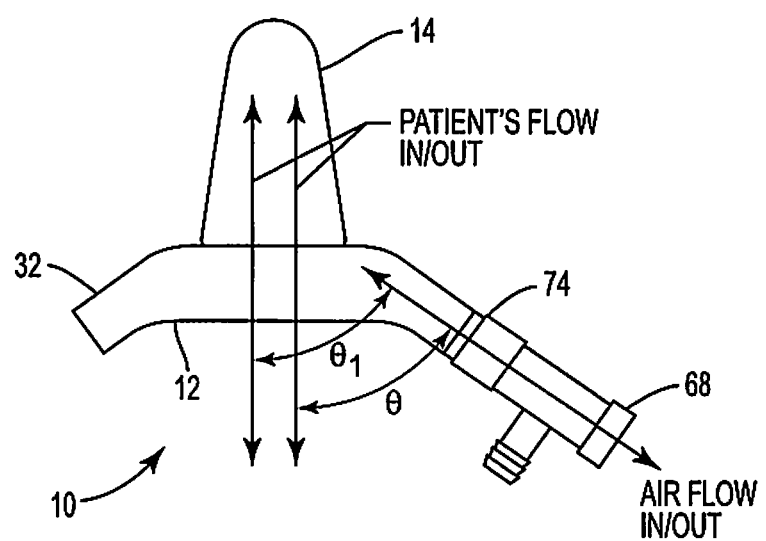
FIG. 16 shows a front perspective view of the inhalation device shown in FIG. 1.

A primary gas fluid supply 18 is connected to inhalation unit 12 by tubing 20. A primary gas, such as oxygen, is combined with a second gas, such as ambient air, to generate a larger total gas flow. This total gas flow post air entrainment is set at an angle of about 35 and about 70 degrees to the longitudinal axis. This achieves the benefit of isolating the "Venturi® Jet" from increased backpressure build up due to forced exhalations, coughing and pursed lip breathing which would interfere with said Venturi® Jet's ability to function properly and would thus as is seen in prior art cause inaccurate oxygen percentages to be sent and then inhaled by the subject. Said angulations are from about 35 and about 70 degrees to said longitudinal axis. The benefit derived from the angle keeping the Venturi® jet about 35 to about 70 degrees off the longitudinal axis is such that backpressure on the Venturi® Jet is not had as the Venturi® jet is isolated off the line, as seen in prior art, where the Venturi® Jet, which is responsible for air entrainment generating high flow rates of pre-mixed oxygen to air is had perpendicular to the patient's breathing orifices. This benefit is further illustrated in FIG. 16, which depicts the direction of air flow from the patient as relates to that from the Venturi® jet. The airflow from the Venturi® jet and the patient are disposed at depicted angles θ and θ₁. The airflow directed off and out the patients nares, e.g. the location outside the opening of nostrils, is disposed to angles 55 to 90 degrees, due to a combination of the anatomic positioning of the nares and the inventions angles. As such the Venture® jet is removed and unaffected by nasal exhaled flow. While exhaled and pursed lip breathing, and or coughing is directed perpendicular out of the patients at 82 to 100 degrees with a primary exit flow mean at 86-88 degrees but has zero effect on the Venturi® jets functioning. This due to the design as the Venture® jet is set above the upper lip further removed from exhaled flow exiting ones mouth. Because the patient's airflow is not directly in line with the O₂/air flow from the Venturi® jet, it does not create the backpressure effects seen in prior art devices. This lack of backpressure then keeps a constant flow rate of the oxygen at a consistent concentration to the patient, unlike as seen in prior art devices previously. This configuration of the present invention also does not dry out the nasal passageways of the patient, since the air flow is not directly impacting the nares, and the patient quite literally inhales form a fresh, always available replenished gas reservoir of a set and precise oxygen concentration which is due to the offset positioning of the Venturi® jet from the patient's breathing path. As a result, there will be reduced or no cracking and/or bleeding of the nasal passages, making the patient more comfortable, also eating will be able to be accomplished without any interruption in precise required oxygen concentrations, which is unlike the prior art where oxygen masks need to literally be removed from the patient when eating.

The longitudinal axis is oriented substantially perpendicular to the nose hood within inhalation unit 12 and then passed across an area below the nasal passages for inhalation according to the subject's breathing pattern. The gas mixture now perpendicular can also be directed towards the mouth of the subject such that the blended gases may be inhaled orally by the user. It is envisioned that various primary and secondary gases may be employed. It is further envisioned that various percentages of gas mixture may be used, ranging from 0-100% for each gas depending on the particular inhalation application. It is contemplated that three or more gases, or only a single gas, may be administered via inhalation device 10.

Referring to FIGS. 3-6, tubular inhalation unit 12 includes a mixing section 22 in which the gases are mixed, and an inhalation chamber 24 through which the mixed gases flow for inhalation by the user. Inhalation chamber 24 is disposed below the nasal passages of the subject in a configuration such that the mixed gases passing through chamber 24 are inhaled through the nasal passages ascending to the breathing pattern of the subject, as shown by arrows A. This configuration of device 10 advantageously avoids the negative effects associated with forcing gas directly into the nasal passages and/or structures that divert gas flow directly into the nasal passages. Inhalation chamber 24 is symmetrical such that mixing section 22, which is removable from inhalation chamber 24, may be mounted upon either end of the inhalation chamber as may be required by wearer convenience and gas supply location. Inhalation chamber 24 includes a first end portion 31a and a second end portion 31b. End portions 31a and 31b are coaxially disposed about an axis X defined by chamber 24.

Nose hood 14 is mounted to the middle section of inhalation chamber 24, and is formed of a semi-rigid material, such as, for example, polyvinyl chloride, such that it overlies the wearer's nose and is open at its bottom. Resilient metal band 26 is mounted within nose hood 14 along a central peak 28 thereof. Band 26 may be shaped as required to assist in retaining nose hood 14 and supporting unit 12 with the nose of the subject.

Inhalation chamber 24 has a central area 30 disposed below nose hood 14, as shown in FIG. 4. End portions 31a and 31b taper to a circular cross-section at ends 32 and 34, respectively. It is contemplated that ends 32, 34 may have alternative cross-sections. It is further contemplated that chamber 24 may have other cross-sectional configurations, such as, circular, elliptical, etc. Ends 32, 34 are disposed at an angle of about 40° to about 50° from the X-axis of central area 30 of chamber 24. Ends 32, 34 may be disposed at various angular orientations according to the particular application. It is still further contemplated that ends 32, 34 may also include a swivel pivot 87, 88, to allow for rotation about the x-z axis of about 0° to about 65°, preferably about 10° to about 40°, more preferably about 20° to about 35°, as shown in FIG. 5. Ends 32, 34 may also include connections 85, 86, for removably connecting tubular body 52 on either side of ends 32, 34.

Nose hood 14 is configured for disposal about the nose of the subject. Nose hood 14 includes a surface 15 configured to engage the face of the subject. Cavity 14a of nose hood 14 communicates with chamber 24 such that during inhalation of gas according to the subject's breathing pattern, the mixture passes to cavity 14a for inhalation through the nasal passages of the subject. It is contemplated that the gas mixture may be inhaled in various patterns. Surface 15 engages the face to substantially seal fluid flow from passing outside of the conduit between chambers 24 to cavity 14, or from undesired ambient air flow entering cavity 14a. This advantageous configuration prevents inhalation of undesirable fluid. It is contemplated that nose hood 14 may be employed without surface 15 engaging the face such that nose hood 14 is loosely attached to the subject.

Nose hood 14 is provided with a pair of inwardly directed ledges 36 along its bottom edges 38. Depending from ledges 36 are flange members 40, which engage the opposed edges of upwardly directed aperture 42 formed in central area 30 in inhalation chamber 24. Aperture 42 is disposed in flush alignment with an upper wall 42a of central area 30. Aperture 42 faces the nose of the subject in a configuration such that the mixed gas of the fluid path, along axis X, is inhalable from central area 30 with the nose.

In addition to aperture 42, which allows the mixed gasses to be inhaled through the nose, central chamber area 30 includes apertures 44. Apertures 44 have a scoop configuration, which is designed to divert the mixed gas flow to an area adjacent the mouth of the subject. In addition to providing for inhalation through the nasal passages, the advantageous design of device 10 provides for inhalation of the mixed gases through the mouth.

Apertures 44 include openings 44a respectively, disposed within inhalation chamber 24. Apertures 44 are configured to receive and divert the mixed gas flow downward through openings 44b of chamber 24, as shown by arrows B. Apertures 44 are configured to oppositely direct and divert gas flowing from either end of unit 12. The scoop diverters of apertures 44 direct a portion of the mixed gases downward toward the subject's mouth so that the subject may inhale the mixed gases. Apertures 44 project slightly into central area 30 so as to cause negligible turbulence and back pressure to the gas passing through chamber 24. In addition to apertures 44, a central aperture 46 may be located on the lower surface of chamber 24 to help minimize backpressure effects of exhaled air from the nose. Openings 44a and 44b can be conical, oblong, elongate, oval, elliptical, tapered, funnel-shaped, pointed, pyramidal, or other shape and are configured so as to be adjustable and rotatable in order to direct and divert gas flow toward or away from the nasal passage of a subject and toward the lips using the device over a wide range of degrees. One embodiment of the present invention is configured so that the sleeve having the openings 44a and 44b can be adjusted incrementally over about 180 degrees. Other embodiments having a reduce range of adjustment are also possible.

As shown in FIGS. 5 and 6, apertures 44 are disposed on alternate sides of axis X such that they are opposing and offset within chamber 24. It is contemplated that apertures 44 may be aligned with axis X in chamber 24 and/or facing the same direction.

Referring to FIGS. 7-12, mixing section 22 is configured such that oxygen or other primary fluids are mixed with a second fluid, for example ambient air. Mixing section 22 includes a mixing chamber portion 48, a Venturi® nozzle unit 50 and a sleeve, such as, for example, an adjustment collar 74. Mixing chamber 48 is composed of a tubular body 52 having a first, externally threaded end 54 and a second internally threaded end 56.

Hollow stub section 58 projects outwardly from tubular body 52, and communicates with the interior of body section 52. Section 58 is provided with ridges 60 to facilitate connection of gas tube 20. Venturi® nozzle unit 50 includes a central stub 62 ending in nozzle end 64 and having right angle bore 66. Central stub 62 is provided with a threaded finger grip portion 68 at its distal end, which allows stub 62 to be inserted into tubular body section 52. Right angle bore 66 is located on stub 62 such that when the stub is fully inserted and tightened into mixing chamber 48, end 70 of bore 66 aligns with bore 72 in stub 58 to allow the primary fluid to pass through nozzle end 64.

Mixing chamber 48 includes bore 80 through its side, which communicates with the interior of mixing chamber 24. Bore 80 is located within recessed portion 76 upon which collar 74 is disposed. As shown in FIGS. 8 and 9, detents 78 contact nub 82 on the mixing chamber body to allow collar 74 to slidably adjust the effective size of bore 80 by virtue of the degree of overlap between bore 80 and aperture 84 in collar 74. In this manner, the amount of ambient air passing into mixing chamber 48 is regulated. For example, in FIG. 8, port 80/84 is rotatable to the partially open position. In FIG. 9, port 80/84 is in the fully closed position. Port 80/84 may be adjusted between an open position and the fully closed position. Bore 80 is disposed proximal to nozzle end 64 when Venturi® nozzle unit 50 is in place. It is envisioned that collar 74 may be alternatively manipulated to regulate the amount of ambient air passing through bore 80, such as by a preset orientation, which is axially slid into recessed portion 76. It is further envisioned that port 80/84 may be processor controlled using associated electronics as is known to one skilled in the art.

As shown in FIGS. 11 and 12, Venturi® unit 50 is interchangeable with mixing section 22 and can be modified to flow rate requirements for a particular inhalation application. Venturi® unit 50 may include various alternate embodiments of bore 66, which include alternate diameter bores corresponding to different flow rates of the primary fluid without the necessity of adjusting tank pressure. The bore of Venturi® unit 50, as shown in FIG. 11, for example, has a greater diameter than the bore of Venturi® unit 50 shown in FIG. 12. The larger diameter of bore 66 in FIG. 11 allows for a greater flow rate of primary fluid for a given source pressure. Accordingly, the bore of Venturi® unit 50 shown in FIG. 12 allows for lower flow rate applications. Device 10 advantageously includes the capacity of interchangeable Venturi® unit 50 such that unit 12 may be employed with various rate gas flow applications.

In use, inhalation unit 12 is prepared by installing mixing section 22 with inhalation chamber 24 by threading end 54 into the desired threaded end (32 or 34, 34 as shown in FIG. 3) of chamber 24. The appropriate Venturi® unit 50 for the gross flow rate desired is installed in mixing section 22 and the resulting unit 12 is affixed to nose hood 14. Device 10 is disposed with the subject's head, as shown in FIGS. 1 and 2. Unit 12 is connected to a primary oxygen supply 18 by tube 20 connected to stub 58. A continuous flow of oxygen is initiated. The relatively high velocity exit of the oxygen from nozzle end 64 in the area of bore 80 causes a reduced pressure area to be created, thus drawing in ambient air through bore 80. The ratio of ambient air to oxygen may be adjusted and controlled by setting of adjustment collar 74, as described above. By mixing the oxygen with ambient air there is no need for further humidification of the gas mixture.

The resulting air/oxygen mixture travels to end 34 and then to central area 30 through inhalation chamber 24, along axis X, for exit through the opposite end 32 of chamber 24. As the gas mixture passes aperture 42, it may be inhaled therefrom by the subject through the subject's nostrils according to the subject's breathing pattern and/or a desired inhalation activity, as described above. The subject inhales the fluid in a direction perpendicular, along axis Y, to the flow of fluid, along axis X, from central area 30.

Apertures 44 divert a portion of the mixed gas flow downward such that it passes in front of the mouth of the subject to be inhaled. The angular offset of the ends 32, 34 of inhalation chamber 24 allows a negligible fluid flow to impinge upon the nasal tissues, thus providing a desired tactile indication that the unit is operating. This angle, however, is not so great as to cause the subject the uncomforting as well as drying effects of direct impingement of the flowing gas upon the nasal membranes. The angle also adapts unit 12 to the facial contours of the subject and lessens the backpressure effects of apertures 44. The offset is not great enough to create significant backpressure effects on mixing section 22 by the subject's breathing.

In an alternate embodiment, as central chamber 30 is symmetrical about a vertical axis Y, mixing section 22 may be installed on either end thereof to accommodate subject preferences and for convenience in access to the primary fluid supply. Accordingly, the mixed gas supply would travel from end 32 towards end 34. Unit 12 may be constructed of appropriate plastics such that it is both lightweight and easily replaced and sterilized.

In another alternate embodiment, inhalation chamber 24 is fabricated from a flexible material, such as ribbed plastic, etc., which can be manipulated into various orientations. For example, flexible chamber 24 is manipulable and relatively pivotable about axis Y. This configuration allows bending of end 32 and/or end 34 about axis Y to facilitate fitting unit 12 about the subject's face and/or facilitating the connection with a gas supply. This advantageously aids comfort and adaptability.

Figure 13:
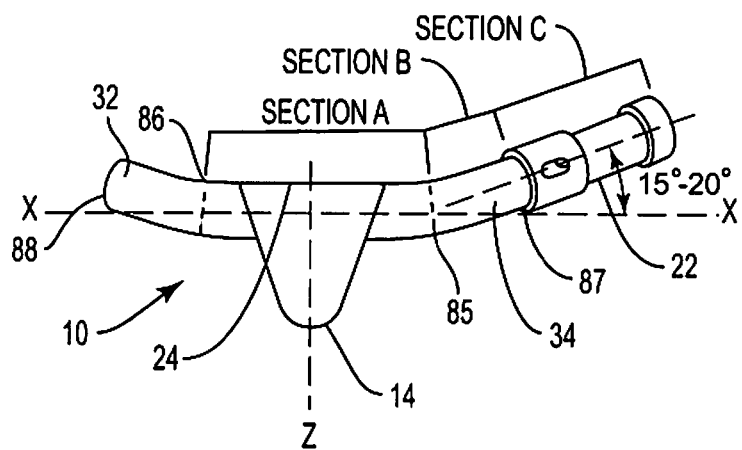
FIG. 13 shows a detail view of an alternate embodiment of the inhalation device shown in FIG. 5.
Figure 14:
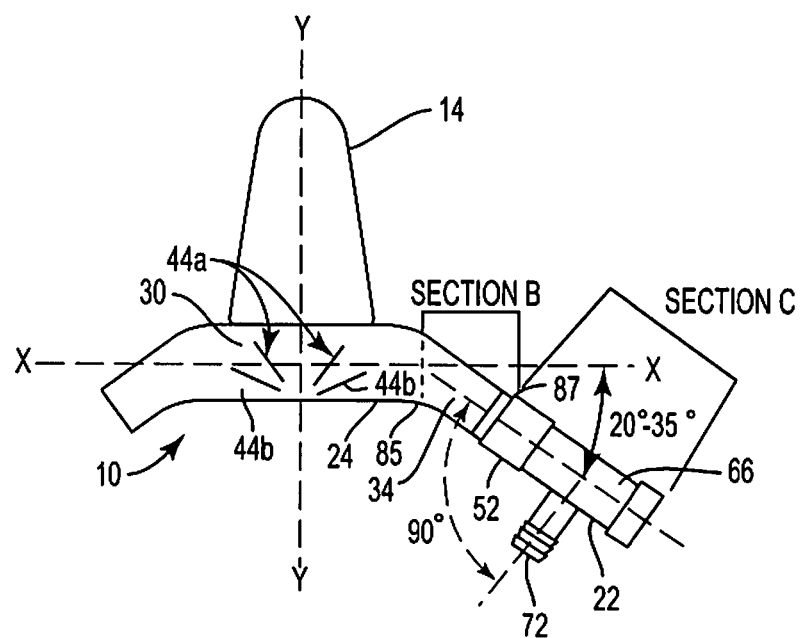
FIG. 14 shows a detail view of an alternate embodiment of the inhalation device shown in FIG. 3.
Figure 15:
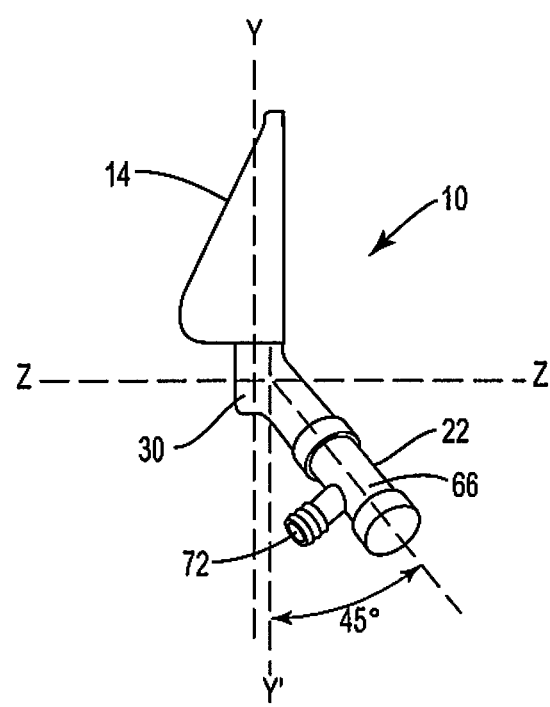
FIG. 15 shows a detail view of an alternate embodiment of the inhalation device shown in FIG. 4.

The inhalation device 10 can comprise three sections A, B and C, as shown in FIGS. 13-15. Section A contains the nose hood 14, inhalation chamber 24, central area 30 and ends 32 and 34. Section B contains is bounded by connections 85, 86 and swivel pivots 87,88. Section C contains mixing section 22. Section B is rotatable, and allows the physician to isolate the valve of section C from backpressure. In FIG. 13, section C can be at an angle of about 0° to about 65°, more preferably, from about 15° to about 25° from depicted axis x. In addition, this adds to patient comfort. Section B is for example, a sleeve, ball valve, or flexible tube among other things. Section B is configured to be removed and transposed to the opposite side for convenience, comfort and proximity to an oxygen source. For example, instead of draping a long oxygen tube from section B to the oxygen source, it is possible to remove section B and reattach it on the other side to gain better proximity to an oxygen source to reduce the elongated tubing for access.

It is additionally contemplated that tubular body 52 is disposed at an angle of about 20° to about 35° with respect to the x-axis of central area 30 of chamber 24, and disposed at angle of about 90° from right angle bore 66, as depicted in FIG. 14.

It is further contemplated that bore 66 is disposed at an angle of about 45° relative to bore 72, as depicted in FIG. 15.

In yet another embodiment of the present invention, the inhalation device is configured to have a rotating disc that can be interchanged with particular tubes having a range of different outflow diameters (i.e., ~22 mm). The tubes may be made from a length of light plastic or other flexible material, and configured so as to taper toward its specific exit diameter. The tubes are joined together by a rotating disc. The rotatable disc, together with the tube and narrowed outflow diameter are placed at stub 62 as the jet exit diameter with bore 66, extending rearward toward finger grip portion 68. Bore 66 is joined to the incoming source gas tube and the tube is configured to have a slot that aligns with the bore so that the source gas can enter the extended tube. This allows for interchanging tubes of different diameters in order to better control the gas flow rates according to the patient's needs.

While the invention has been illustrated and described in detail in the drawings and foregoing description, the same is to be considered as illustrative and not restrictive in character, it being understood that embodiments have been shown and described and that all changes and modifications that come within the spirit of this invention are desired to be protected.

What is claimed is:

1. An inhalation device, comprising:
 a nose hood having an opening, the nose hood defining a cavity and a vertical axis;
 a chamber connected with the nose hood and including a first end portion, a second end portion, and a central portion, the central portion defining a longitudinal axis being oriented substantially perpendicular to the vertical axis, the first end portion and the second end portion being coaxially disposed about the longitudinal axis, wherein the first end portion extends to a first end of a chamber and the second end portion extends to a second end of the chamber, the first end and the second end each being angularly offset from the longitudinal axis; and
 a mixing section connected with either of the first end or the second end, and at least one fluid, wherein the mixing section delivers the at least one fluid to the first end in a fluid flow path configured to travel in a direction along the longitudinal axis and exit the chamber from the second end;
 wherein the central portion defines at least one opening disposed in flush alignment with an upper wall of the central portion in a configuration such that the at least one fluid of the fluid flow path is inhalable from the central portion into the nose hood.

2. The inhalation device of claim 1, wherein the first and the second ends are angularly offset by an angle of about 35 degrees to about 45 degrees from the longitudinal axis.

3. The inhalation device of claim 1, wherein the chamber defines at least one scoop configured to divert the at least one fluid of the fluid flow path for inhalation.

4. The inhalation device of claim 3, wherein the chamber defines a pair of opposing scoops being offset relative to the longitudinal axis of the central portion.

5. The inhalation device of claim 1, wherein the mixing section delivers a plurality of fluids including oxygen provided via a nozzle and ambient air provided via a bore defined in a mixing chamber of the mixing section.

6. The inhalation device of claim 5, wherein the plurality of fluids include oxygen provided via a high velocity nozzle across a bore defined within the mixing section causing a fluid pressure drop adjacent the bore such that ambient air is drawn into the mixing section, whereby the oxygen is mixed with the ambient air.

7. The inhalation device of claim 6, wherein an amount of ambient air drawn through the bore is regulated via a sleeve disposed about the mixing section.

8. The inhalation device of claim 7, wherein the sleeve is threadably engageable with the mixing section in a configuration for regulating the ambient air drawn through the bore.

9. The inhalation device of claim 5, wherein said nozzle is designed to have the plurality of fluids pass via a right angle to a decreased diameter channel to provide greater acceleration of the incoming plurality of fluids.

10. The inhalation device of claim 9, wherein said nozzle is interchangeable with another nozzle having a different decreased diameter channel.

11. The inhalation device of claim 1, wherein the first end and the second end are relatively pivotable about the vertical axis.

12. A method of providing gas flow to a patient, comprising:
   placing the nasal hood-defining cavity of the inhalation device of claim 1 on a patient in need of breathing aid; and
   positioning the gas flow post air entrainment of said chamber at an angle of about 35 to about 70 degrees with respect to the longitudinal axis so as to provide a fluid flow path that is inhalable from said central portion.

13. The inhalation device of claim 1, wherein the first end portion of the chamber and the second end portion of the chamber are configured so as to be interchangeable with one other.

14. An inhalation device, comprising:
   a nose hood defining a cavity;
   a chamber connected with the nose hood having a central portion, the central portion defining a longitudinal axis, said chamber configured to receive incoming gas flow post air entrainment at an angle of between about 0 and about 70 degrees with respect to the longitudinal axis, said chamber being oriented substantially perpendicular to the nose hood; and
   a mixing section being connected with the chamber and at least one fluid, wherein the mixing section delivers the at least one fluid to a first end portion of the chamber in a fluid flow path configured to travel in a direction along the longitudinal axis of the central portion and exit the chamber from a second end portion thereof, the first end portion and the second end portion being coaxially disposed about the longitudinal axis of the chamber;
   wherein
   the central portion defines at least one opening such that the at least one fluid of the fluid flow path is inhalable from the central portion into the nose hood;
   the first end portion of the chamber and the second end portion of the chamber are configured so as to be interchangeable with one other; and
   the second end portion includes a second end, which is angularly offset from the longitudinal axis of the central portion.

15. A method of providing gas flow to a patient comprising:
   placing the nasal hood-defining cavity of the inhalation device of claim 14 on a patient in need of breathing aid; and
   positioning the gas flow post air entrainment of said chamber at an angle of about 35 to about 70 degrees with respect to the longitudinal axis so as to provide a fluid flow path that is inhalable from said central portion.

16. The inhalation device of claim 14, wherein the mixing section is configured to deliver a plurality of fluids to the first end portion;
   wherein the plurality of fluids include oxygen provided via a nozzle and ambient air provided via a port defined with the mixing section;
   wherein said nozzle is designed to have the plurality of fluids pass via a right angle to a decreased diameter channel to provide greater acceleration of the incoming plurality of fluids.

17. The inhalation device of claim 16, wherein said nozzle is interchangeable with another nozzle having a different decreased diameter channel.

18. An inhalation device, comprising:
   a nose hood defining a cavity;
   a chamber connected with the nose hood and including a central portion being disposed below the nose hood, the central portion defining a longitudinal axis, said chamber configured to receive incoming gas generating a total gas flow post air entrainment at an angle of between about 35 and about 70 degrees with respect to the longitudinal axis, said chamber being oriented substantially perpendicular to the nose hood; and
   a mixing section connected with the chamber and at least one fluid, wherein the mixing section delivers the at least one fluid to a first end portion of the chamber in a fluid flow path configured to travel in a direction along the longitudinal axis of the central portion and exit the chamber from a second end portion thereof, the first end portion and the second end portion being coaxially disposed about the longitudinal axis of the chamber;
   wherein the central portion defines at least one opening such that the at least one fluid of the fluid flow path is inhalable from the central portion into the nose hood; and
   wherein the second end portion includes a second end, which is angularly offset from the longitudinal axis of the central portion.

19. The inhalation device of claim 18, wherein the first end portion includes a first end, which is angularly offset from the longitudinal axis of the central portion.

20. The inhalation device of claim 18, wherein the chamber defines at least one scoop configured to divert the at least one fluid of the fluid flow path for inhalation.

21. The inhalation device of claim 20, wherein the chamber is configured to define a pair of opposing scoops being offset relative to the longitudinal axis of the central portion.

22. The inhalation device of claim 18, wherein the mixing section is configured to deliver a plurality of fluids to the first end portion.

23. The inhalation device of claim 22, wherein the plurality of fluids include oxygen provided via a nozzle and ambient air provided via a port defined with the mixing section;
   wherein said nozzle is designed to have the plurality of fluids pass via a right angle to a decreased diameter channel to provide greater acceleration of the incoming plurality of fluids.

24. The inhalation device of claim 22, wherein the device further comprises a high velocity nozzle configured so as to be in position across a bore defined within the mixing section causing a fluid pressure drop adjacent the bore such that ambient air is dawn into the mixing section, whereby the oxygen is mixed with the ambient air.

25. The inhalation device of claim 24, wherein the device further comprises a sleeve disposed about the mixing section so as to regulate an amount of ambient air drawn through the bore and with the mixing section.

26. The inhalation device of claim 23, wherein said nozzle is interchangeable with another nozzle having a different decreased diameter channel.

27. The inhalation device of claim 18, wherein the nose hood defines a vertical axis, and the first end portion and the second end portion are relatively pivotable thereabout.

28. An inhalation device as defined in claim 18, wherein the at least one opening of the central portion is in flush alignment with an upper wall of the central portion.

29. A method of providing gas flow to a patient, comprising:
   placing the nasal hood-defining cavity of the inhalation device of claim 18 on a patient in need of breathing aid; and positioning the gas flow post air entrainment of said chamber at an angle of about 35 to about 70 degrees with respect to the longitudinal axis so as to provide a fluid flow path that is inhalable from said central portion.

30. The inhalation device of claim 18, wherein the first end portion of the chamber and the second end portion of the chamber are configured so as to be interchangeable with one other.

\* \* \* \* \*